United States Patent [19]
Anderson

[11] Patent Number: 5,824,023
[45] Date of Patent: Oct. 20, 1998

[54] RADIATION-DELIVERY DEVICE

[75] Inventor: Richard Rox Anderson, Lexington, Mass.

[73] Assignee: The General Hospital Corporation, Boston, Mass.

[21] Appl. No.: 633,367

[22] Filed: Apr. 16, 1996

Related U.S. Application Data

[60] Provisional application No. 60/005,289 Oct. 12, 1995.
[51] Int. Cl.⁶ .................................................. A61N 21/00
[52] U.S. Cl. .............................................................. 607/88
[58] Field of Search ..................................... 128/664, 665; 606/2, 13–19; 607/88–94; 600/473–476

[56] References Cited

U.S. PATENT DOCUMENTS

| | | |
|---|---|---|
| 3,527,932 | 9/1970 | Thomas . |
| 3,602,213 | 8/1971 | Howell et al. . |
| 3,818,914 | 6/1974 | Bender . |
| 4,364,033 | 12/1982 | Hotine . |
| 5,108,388 | 4/1992 | Trokel . |
| 5,309,339 | 5/1994 | Webb . |
| 5,380,317 | 1/1995 | Everett et al. . |
| 5,505,726 | 4/1996 | Meserol . |
| 5,519,534 | 5/1996 | Smith et al. . |

FOREIGN PATENT DOCUMENTS

| | | |
|---|---|---|
| 0 142 250 | 5/1985 | European Pat. Off. . |
| 2148 513 | 5/1985 | United Kingdom . |

OTHER PUBLICATIONS

Copy of International Search Report mailed Jan. 29, 1997.
Anderson, et al., "The Optics of Human Skin," *The Journal of Investigative Dermatology*, 77:13–19 (1981).
"Laser Handpiece Reduces Skin Damage," *Clinica 2836*, p. 22 (Jan. 20, 1988).

*Primary Examiner*—John P. Lacyk
*Assistant Examiner*—Samuel Gilbert
*Attorney, Agent, or Firm*—Fish & Richardson P.C.

[57] ABSTRACT

A method and device for irradiating a material, such as a tissue in a patient, is described. The method features the step of first exposing the tissue with radiation. Following the exposing step, the radiation is partially re-emitted (e.g., reflected or scattered) from the tissue. The re-emitted radiation is then collected and imaged back onto the tissue using an external irradiating device containing, for example, a hemispherically shaped reflective housing. The housing contains a reflective coating disposed on one of its surfaces.

30 Claims, 5 Drawing Sheets

RADIATION-DELIVERY DEVICE

BACKGROUND

This application claims priority from provisional application U.S. Ser. No. 60/005,289, entitled Radiation-delivery Device, filed Oct. 12, 1995.

This invention relates to radiation-delivery devices.

Radiation sources, such as lasers, are used in a variety of medical applications because of their ability to generate precise, self-cauterizing incisions and locally heat tissue without contacting the patient. In particular, laser light is used in a variety of dermatological therapies, such as to remove tatoos, port-wine stains, and unwanted hair. In these applications, radiation is typically delivered through a fiber optic system to a lens, which subsequently images the radiation onto the region of interest. The radiation is absorbed by a portion of the skin or hair (e.g., the melanin or blood vessels), resulting in optical absorption and localized heating.

In nearly all laser-based surgical procedures, it is desirable to maximize the amount of radiation delivered to the tissue, and minimize the amount of radiation which is re-emitted (e.g., reflected or back-scattered) from the tissue. This is particularly difficult to achieve during dermatological procedures, as the turbid optical quality of the skin tends to scatter incident light in all directions. In addition, reflection due to differences in the refractive indices of the skin (n=1.5) and the air (n=1.0) leads to further losses. To compensate for radiation lost through these processes, the operator is forced to increase the output power of the light source. This often decreases the means is a fiber optic waveguide or an articulated arm, and the radiation source is a laser.

In preferred embodiments, the re-emitted radiation is received and reflected by a reflective device to re-expose the material. For example, the reflective device can be a reflective housing positioned proximal to the material prior to the exposing step. Preferably, the reflective housing is substantially hemispherical in shape, and the material is positioned substantially near the center of the hemisphere. Alternatively, the reflective housing is substantially elliptical in shape, and the material is positioned substantially near a focus of the ellipse. The reflective housing may also be substantially spherical in shape, with the opening disposed on a surface of the sphere. In still other embodiments, the reflective housing is substantially cone-shaped and includes an opening at the base of the cone. During operation, the material is positioned near this opening.

The method of the invention can also be carried out with an irradiating device which includes an optically transparent plate featuring a reflective coating on one of its surfaces. The reflective coating is disposed on the plate to transmit normally incident radiation (i.e., radiation angled at between about 80° and 100° relative to the surface of the reflective coating), receive radiation re-emitted from the material, and reflect any re-emitted radiation back onto the material. Preferably, the reflective coating contains a dielectric material or multiple layers of dielectric materials which exhibit angularly dependent reflective properties.

Here, by "substantially hemispherical", "substantially elliptical", or "substantially spherical" is meant a reflective housing which is shaped, respectively, in accuracy of the procedure, or may, in fact, be impossible if the light source is operating at its maximum power output.

Several references teach optical systems which manipulate laser beams to generate more desirable light fields for medical therapies. In U.S. Pat. No. 5,309,339, for example, Webb describes an optical concentrator for manipulating the cross-sectional area and reducing speckle of an incident laser beam. In Webb's device, a spherical or hemispherical mirror is used to return laser light scattered from a diffusely reflective surface back onto the point of incidence. Lenses are then used to produce an output beam by collecting light from the point of incidence.

SUMMARY

In general, in one aspect, the invention provides a method for irradiating a material. The method includes the step of first exposing the material with radiation (e.g., optical radiation). Following the exposing step, radiation is partially re-emitted (e.g., scattered, reflected, or both scattered and reflected) from the material. The material is then re-exposed with the re-emitted radiation. Preferably, the material is a patient's tissue. By "tissue" is meant any collection of cells or any specific organ in the patient (e.g., human skin).

The method of the invention is carried out with an irradiating device configured to receive radiation from a radiation delivery means. The radiation delivery means delivers radiation from a radiation source to the material, and is preferably connected to a reflective housing. The housing includes an opening or surface for placement over the material and a reflective component proximal to the opening or surface. Most preferably, the radiation delivery the form of a hemisphere, ellipse, or sphere so that it reflects incident light to a well-defined area. Preferably, this area is not more that a few millimeters in radius. "Substantially cone-shaped" means at least a portion of the housing is conically shaped. By "center of the hemisphere" is meant the geometrical center of the sphere composed of two identical hemispheres. By "substantially near the center" or "substantially near the focus" is meant a position within a few millimeters of, respectively, the actual center or focus. "Substantially transparent" and substantially reflects" means that, respectively, at least 80% of the radiation is either transmitted or reflected.

The reflective housing preferably includes a reflective coating for reflecting the re-emitted radiation. The coating, for example, may be a reflective film, such as a metallic or dielectric film. The dielectric film may be reflective in only a portion of the electromagnetic spectrum, thereby allowing direct visualization of the material through the film.

In other preferred embodiments, the reflective housing features an array of grooves configured to reflect the re-emitted radiation. These grooves have reflective properties similar to those of corner cubes, retroreflectors, or similar optical components which reflect radiation by internal reflection. Other reflecting materials, such as white paint or reflecting tapes, may be used to reflect radiation within the housing. In these embodiments, the reflective housing may take on any shape. For example, in addition to the embodiments described above, the housing may be formed in the shape of a cylindrical tube, with the reflective material disposed on portions of the tube's inner surface. In this case, the opening for irradiating the tissue is positioned on one of the flat surfaces of the tube.

In preferred embodiments, the irradiation device is used during a medical therapy to irradiate a patient's tissue. In this case, the device is used in combination with standard medical procedures normally employed when radiation is delivered to tissue. Preferably, the radiation used in the therapy is optical radiation, and the therapy is used to treat human skin. Examples of such therapies include optical removal of tatoos, port-wine stains, abnormal blood vessels, psoriatic skin, unwanted hair, pigmented lesions, skin cancers and other lesions treated by laser surgery, phototherapy, photochemotherapy or photodynamic therapy.

The invention has a number of advantages. In particular, it increases the efficiency of a laser-based surgical procedure by treating the tissue of interest with radiation which is normally not utilized. Scattered or reflected light, lost during conventional procedures, is effectively "recycled" and used to re-expose and treat the tissue. In this way, optical fluences can be kept relatively low during treatment, thereby enhancing the accuracy and flexibility of the therapy.

The invention provides a gain of optical energy available to the tissue by a factor of up to $(1-R)^{-1}$, where R is the wavelength-dependent fraction of incident light re-emitted from the tissue. For example, when R is 0.7 (a typical value for red light re-emitted from fair skin) the energy available to the skin using the irradiation device may be as large as three times that available without the device.

In addition to increasing the amount of radiation available for therapy, the invention can also effectively increase the exposure spot diameter of the radiation. In many applications in which the "target" for therapy is deep within the skin (e.g., during the removal of tattoos, port-wine stains, or hair), such a larger exposure spot diameter is advantageous.

Moreover, by collecting and then re-exposing the tissue of interest with the re-emitted radiation, the invention generates a more spatially uniform field during therapy. This gives the operator more control over the amount of heat delivered to the tissue, and thus improves the accuracy of the therapy.

The invention also increases the safety of laser-based therapies. Light reflected or scattered from the tissue, as well as ablated tissue which can be hazardous to the operators, is contained within a well-defined area by the irradiating device. Moreover, the device can be made small and compact, and can be used interchangeably with conventional laser-based surgical instruments. The device can additionally be fabricated with relatively inexpensive, disposable materials; a new, sterilized device can therefore be used for each procedure.

These and other advantages will be apparent from the following detailed description, and from the claims.

DETAILED DESCRIPTION

Device Structure

Figure 1:
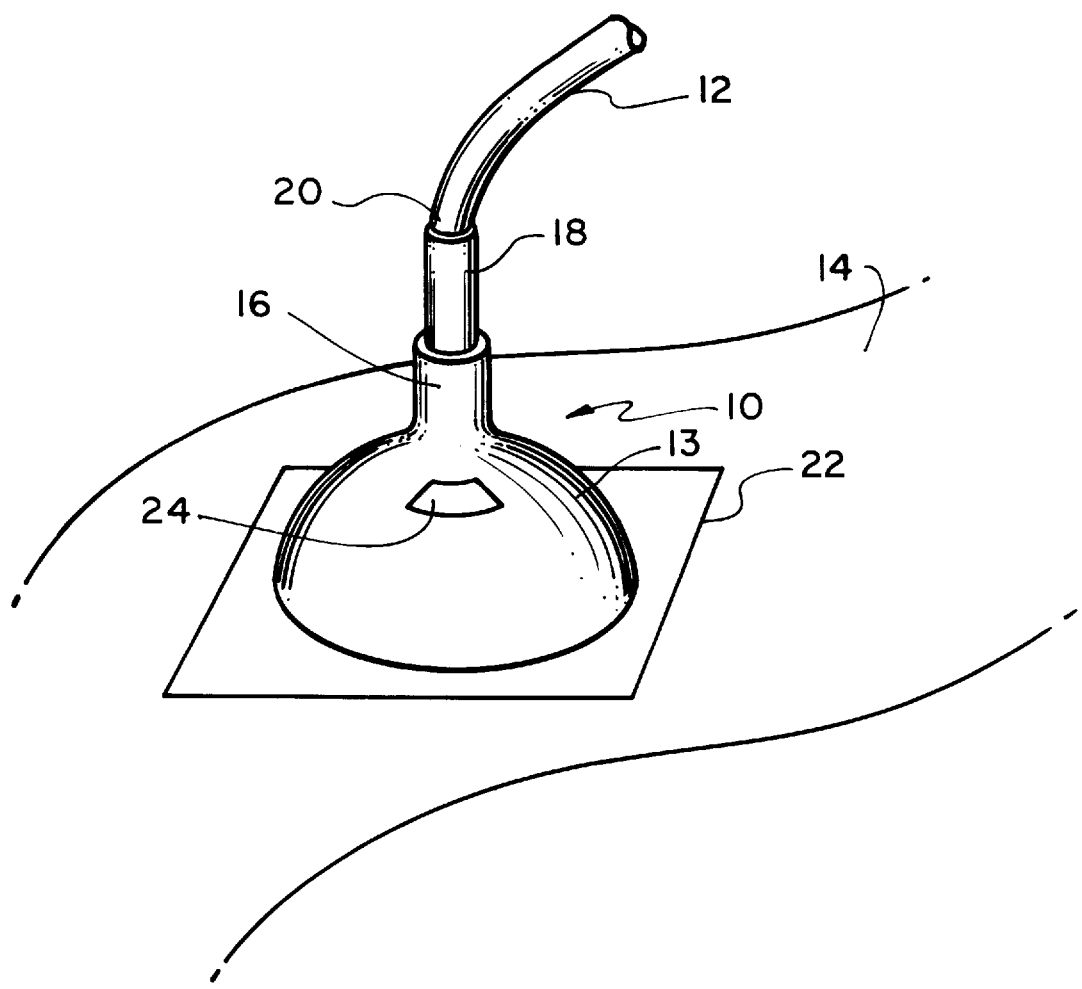
FIG. 1 is a top view of an irradiating device of the invention being used to irradiate a patient's skin.

Referring first to FIG. 1, an irradiating device 10 delivers radiation during a therapy to an area of a patient's tissue 14. The device 10 is configured so that radiation which is normally re-emitted from the tissue after irradiation (and is thus wasted during the therapy) can be collected and imaged back onto the originally irradiated area.

The device includes a fiber optic waveguide 12 coupled to a laser or other radiation source (not shown in the figure). A distal end 20 of the fiber optic waveguide is housed in a delivery handpiece 18 and an input port 16 so that radiation from the fiber can be delivered to the device 10. The input port 16 is connected to a hemispherically shaped reflective housing 13 which surrounds the tissue to be irradiated and is configured to reflect radiation. During operation, radiation is delivered from the fiber optic waveguide 12 to the tissue. Portions of the delivered radiation are either absorbed by the tissue, leading to radiation-induced heating, or are re-emitted from the irradiated area. The re-emitted radiation propagates away from the tissue, and is collected by the hemispherically shaped reflective housing 13. A template 22 connected to the housing 13 is used to position the device on the patient's tissue and facilitate alignment of the radiation. The template is especially useful for aligning radiation onto tissue containing rough or curved surfaces, such as the skin. The reflective housing 13 includes a transparent porthole 24 for viewing the irradiated region.

Figure 2:
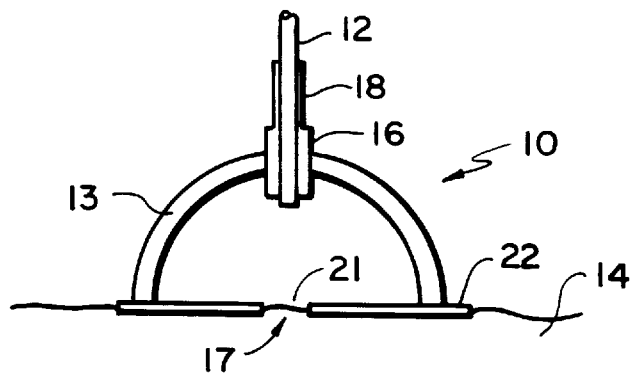
FIG. 2 is a cross-sectional side view of an irradiating device in contact with the patient's skin.
Figure 4A:
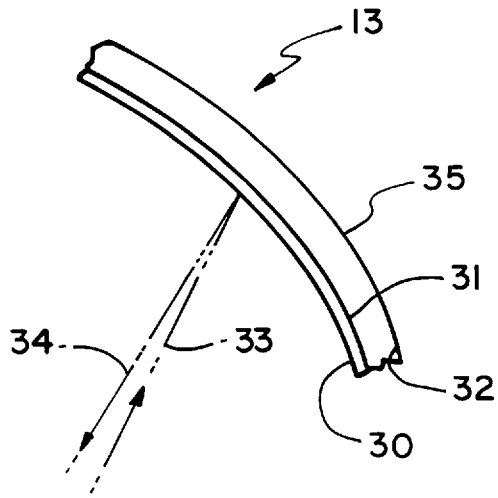
FIGS. 4A and 4B are cut-away cross-sectional side views of, respectively, a reflective housing including a radiation-reflecting coating, and a reflective housing including an array of retro-reflecting grooves.
Figure 4B:
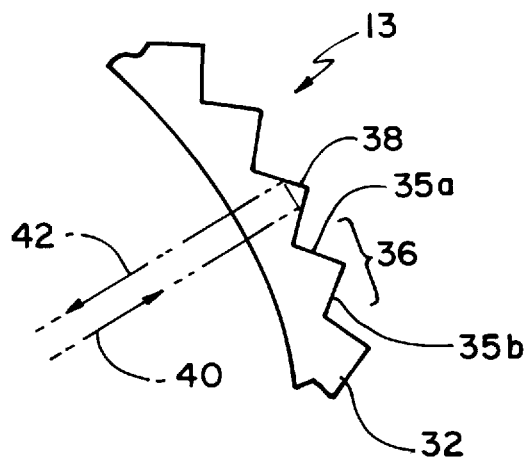

FIGS. 2, 4A and 4B show cross-sectional views of the irradiation device 10 and the reflective housing 13. The delivery handpiece 18 and input port 16 connected to the housing each enclose portions of the fiber optic waveguide 12. The distal end 11 of the waveguide 12 extends into the device and is surrounded by the hemispherically shaped reflective housing 13. The housing 13 is connected to the template 22 which, in turn, is placed in contact with a patient's tissue 14. The template 22 includes an opening 21 positioned above a portion 17 of the tissue and in the center of the hemispherical reflective housing. The opening 21 and distal end 11 of the waveguide are aligned so that, during therapy, radiation from the waveguide passes through the template and onto the tissue.

The reflective housing includes a reflective coating 30 on its inner surface so that during therapy radiation scattered or reflected from the tissue is collected and imaged back onto the originally irradiated portion of tissue. The reflective coating 30 can be any reflective material and can be made using any of a number of techniques known in the art. For example, the coating may be deposited as a thin reflective film on the inner surface of a transparent substrate 32. The coating may also be deposited on the substrate's outer surface.

In particular embodiments, the coating may be a thin metallic film composed of materials such as aluminum, silver, or gold. The reflective properties of these materials are dependent on the material composition and the film thickness, and are well known in the optical arts. Dielectric films may also serve as reflective coatings. These materials have particularly desirable reflectivities at visible and infrared wavelengths, and can be used to coat the inner or outer surfaces of the substrate material 32. Dielectric coatings have the additional advantage that they can be made transparent to visible wavelengths or radiation at certain angles of incidence; thus, when used with transparent substrates, these materials allow the operator to directly view the procedure without the need for a porthole.

The reflective housing is preferably shaped so that re-emitted radiation is collected and imaged onto a region contained in the originally irradiated area. In this way, the spatial extent of the irradiated area is not significantly increased by the reflective process, and thus the accuracy of the procedure is maintained. This is particularly important during therapies requiring small radiation spot sizes, such as during the treatment of small vascularized regions in human skin. As described above, the housing preferably has a hemispherical shape, and the irradiated region is located as close as possible to the center of the hemisphere. In this configuration, the re-emitted radiation incident on the tissue is evenly distributed, and "hot spots" in the irradiated area are avoided.

In the embodiment shown in FIG. 4A, the reflective housing is hemispherical, and radiation (indicated by the arrow 33) incident on the coating 30 is reflected back towards the tissue (arrow 34) with a slight angular deviation. This angle is such that the re-exposed region of tissue lies substantially within the originally exposed area. When the coating 30 is deposited on the outer surface 35 of the substrate 32, radiation reflected back towards the tissue propagates through the substrate twice before re-exposing the tissue.

Referring now to FIG. 4B, the housing can also be made reflective by cutting right-angle grooves 36 into the transparent substrate 32. In this case, each groove 36 has two orthogonal reflective faces 35a, 35b and serves as an individual "corner cube" or "retroreflector" for reflecting the incident radiation. Preferably, an array of concentric grooves, each positioned at different cross-sectional slices of the hemisphere, are cut into the substrate. Other patterns of grooves may also be used. Preferably, in order to maximize the reflectance of the housing, the grooves are spaced together as closely as possible. For total internal reflection to occur at the air/substrate interface 38 of each groove, the substrate must be composed of a material having the appropriate refractive index. Typically, optically transparent materials, such as glasses or plastics having refractive indices greater than 1.4, are suitable.

In the reflective housing 13 shown in FIG. 4B, incident radiation (indicated by the arrow 40) re-emitted from the tissue is reflected back towards its point of origin. The reflected radiation (arrow 42) is displaced by an amount equal to the propagation distance between the two orthogonal faces 35a, 35b of the groove. In this way, the irradiated area of tissue is kept small. Moreover, in the embodiment shown in FIG. 4B, the radiation is reflected by the grooves directly back towards its point of origin regardless of the shape of the reflective housing. Thus, irradiation devices employing reflecting grooves have the additional advantage that they can be formed into arbitrary shapes. This is particularly desirable for irradiating devices configured to irradiate hard-to-reach areas of tissue.

Preferably, in the embodiments described above, the substrate is composed of a material which is transparent to the incident radiation. For example, for visible radiation, the substrate can be composed of transparent glasses, plastics, or other suitable materials known in the art. In particular, plastic materials are desirable, as they can be manufactured in high quantities for relatively low costs. Such materials are formed using techniques well-known in the art, such as injection molding or machining. Irradiation devices, and particularly those made from plastic materials, can be sterilized and are disposable.

In addition to the reflective surfaces shown in FIGS. 4A and 4B, other reflective coatings and devices known in the art can be used with the irradiation device's reflective housing. For example, the substrate can be substantially composed of a reflecting material, thereby obviating the need for inner or outer surface coatings. In particular embodiments, the substrate can be composed of a diffusely reflecting white plastic, frosted glass, or a related material. These materials have lower reflectivities than metallic or dielectric-coated materials, and function essentially as optical "integrating spheres." Materials of this type have the advantage of irradiating an area with a particularly uniform field after reflecting the re-emitted radiation.

In other embodiments, the reflecting housing may be covered on its inner or outer surface with reflecting tape, paint, or any other material which can be used to reflect radiation, and particularly optical radiation. Preferably, the reflecting material reflects at least 80% and most preferably, at least 90% of the re-emitted radiation. Since the most preferred applications involve the use of optical radiation, the coating preferably exhibits the above-mentioned reflectivities for wavelengths in the range of 200 nm to 5 microns. In particularly preferred embodiments, the reflective housing is configured to reflect optical wavelengths which are typically used in dermatological applications, i.e., 500–1100 nm.

In still other embodiments, the template connected to the housing can be replaced with a plate which is transparent to the incident radiation. Like the template, the transparent plate is used to position the device on the patient's tissue and facilitate alignment of the radiation. The plate is particularly effective in aligning radiation onto tissue containing rough or curved surfaces, such as the skin.

Figure 3A:
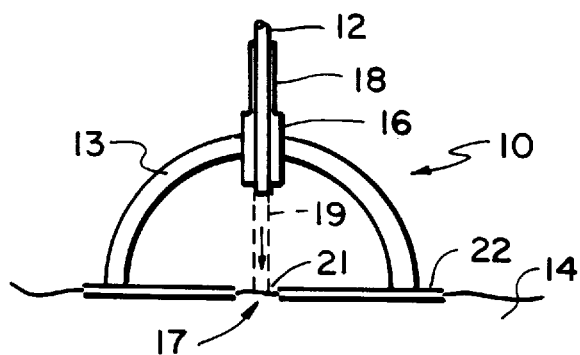
FIGS. 3A–3C are, respectively, cross-sectional side views of the irradiating device during initial irradiation of the skin, after radiation is initially re-emitted from the skin surface, and after the re-emitted radiation is reflected off the reflective housing and back towards the skin surface.
Figure 3B:
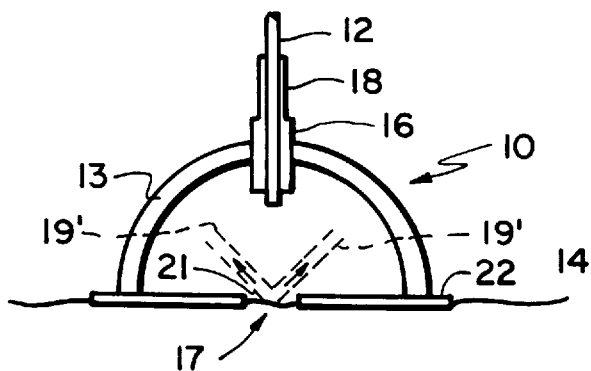
Figure 3C:
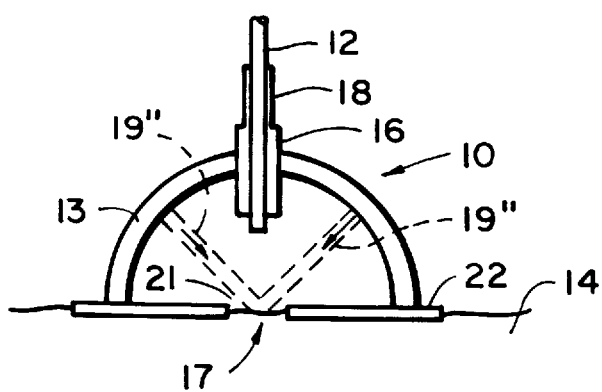

FIGS. 3A–3C illustrate in more detail the propagation characteristics of the radiation during a typical therapy. After being delivered from the fiber optic waveguide 12, incident radiation 19 enters the irradiation device, propagates through the opening 21 in the template 22, and irradiates the portion 17 of the patient's tissue 14. While some of the radiation is absorbed, refractive index differences between the surrounding air (n=1) and the tissue (typically n=1.5) cause a substantial fraction 19' of the incident radiation to be reflected. For example, for both black and white human skin, between 4% and 7% of optical radiation from 250 and 3000 nm is reflected off the stratum corneum (i.e., the skin's upper layer). This same air/skin interface also scatters incident radiation away from the skin's outer surface. Optical scattering within the skin, such as scattering from collagens in the dermis, cells in the epidermis, and other skin structures, additionally directs radiation away from the originally irradiated area.

Radiation propagating away from the tissue surface is collected by the reflective housing 13. Reflection off the housing redirects the re-emitted radiation 19" back towards the tissue surface, where it irradiates the same or nearby region within the originally irradiated area. Here, radiation is again partially absorbed and partially re-emitted. Although a single reflection is indicated in the figures, radiation may undergo multiple reflections in the housing before being reflected back towards the originally irradiated area. As described above, to keep the irradiated area at a minimum, the reflective housing preferably has a hemispherical shape, with the irradiated region positioned at the hemisphere's center.

In theory, this iterative process of exposing and re-exposing the tissue is repeated until all the radiation propagating in the irradiation device 10 is absorbed. In practice, however, losses due primarily to the reflectivity of the reflective housing and the fact that some components in the irradiation device (e.g., the fiber optic waveguide and the porthole) are non-reflective result in finite increases (i.e., gain) in the amount of delivered radiation. Typically, the gain due to the irradiation device represents between about 25% and 300% of the amount of radiation orginally delivered to the tissue. This gain will depend on the wavelength, tissue properties, device reflectance, device size, and device shape.

The actual gain in the radiation energy is determined by comparing the method according to the invention to conventional means for delivering radiation to tissues. In procedures where the irradiating device is not used, the energy $E_0$ of the radiation available for treatment is:

$$E_0 = E_{incident}(1-R_s) \qquad (1)$$

where $R_s$ is a coefficient indicative of the amount of radiation re-emitted from the tissue and $E_{incident}$ is the energy of the incident radiation. $R_s$ is wavelength-dependent and has a value which is less than one: a low value of $R_s$ means that the majority of incident radiation is absorbed by the tissue, while a high value indicates a large amount of radiation re-emission. Thus, if $R_s=0.3$, then $E_0=0.7\ E_{incident}$, meaning that 70% of the incident light is absorbed by the tissue during treatment.

The radiation energy E available for therapy when the irradiation device is employed can be expressed mathematically as:

$$E = E_0[1 + R_sR_m + (R_sR_m)^2 + (R_sR_m)^3 + \ldots] = \frac{E_0}{(1-R_sR_m)} \qquad (2)$$

where $R_s$ and $E_0$ are the quantities expressed above and $R_m$ is the collective reflectance of the reflective housing. Like $R_s$, $R_m$ is wavelength-dependent and has a value less than one. By comparing equations 1 and 2, the gain due to the irradiation device is expressed as:

$$\text{gain} = \frac{1}{(1-R_sR_m)} \qquad (3)$$

Thus, using the device of the invention, the amount of radiation available for therapy increases as the collective reflectance of the reflective housing increases. Most preferably, therefore, this reflectance is made as high as possible.

Table 1, shown below, lists the increases in available optical radiation as a function of the radiation wavelength and the tissue remittance for human skin. In all cases, $R_m$ is 0.9 and $R_s$ is the reflectance value of the skin at the optical wavelength. Increases in optical energy are calculated relative to conventional therapies performed without the irradiating device.

TABLE 1

Gain as a Function of Skin Remittance and Optical Wavelength

| Wavelength (nm) | Application | $R_s$ | Gain | Increase in Optical Energy |
|---|---|---|---|---|
| 510–532 | vascular treatment, tattoo and hair removal | 0.3 | 1.37 | 37% |
| 585 | vascular treatment | 0.3 | 1.37 | 37% |
| 694 | tattoo and hair removal, pigment treatment | 0.7 | 2.70 | 170% |
| 1064 | tattoo and hair removal | 0.6 | 2.17 | 117% |

From Table 1, it is evident that the gain of the radiation increases with the $R_sR_m$ product. This product can be increased by choosing an irradiating wavelength which is re-emitted strongly by the tissue or, as described above, by maximizing the reflectance of the reflective housing for the irradiating wavelength.

As is evident from the Table, optical radiation near 700 nm is subjected to a gain of approximately 170% when used in combination with the irradiating device. This wavelength is easily obtainable using conventional light sources (e.g., ruby, dye, diode and Ti:sapphire lasers). Thus, when used with these light sources, the irradiating device effectively triples the effective amount of radiation available for therapy. Optical radiation at 1064 nm (a wavelength generated using conventional Nd:YAG lasers) is also subject to a high gain (117% increase) when used in combination with the irradiation device.

During therapy, the distribution of radiation reflected from the irradiated area of tissue towards the reflective housing is typically diffuse. This is particularly true for skin, which is an isotropic medium functioning essentially as a Lambertian reflector. In this case, the intensity of re-emitted light varies as $\cos(\ominus)$, where $\ominus$ is the angle relative to the normal vector of the skin surface. However, the amount of light collected by a hemispherical reflector varies as $\sin(\ominus)$. Therefore, the contribution of a hemispherical reflector is most pronounced at $=45°$, i.e., the angle where the product $\sin(\ominus)\cos(\ominus)$ is maximized. This means that although a large fraction of radiation is gathered at angles of between about 0° and 60° from the beam path of the incident radiation, the most significant region of reflected radiation typically occurs at 45° from the angle of incidence. The amount of radiation reflected at 90° from the angle of incidence is typically negligible. Thus, it is particularly important for the reflective housing to have adequate reflective properties in the regions where the reflected radiation is concentrated (i.e., around 45° from the angle of incidence and preferably the region of 0–60°). Coatings in the regions of low radiation concentrations (e.g., 90°) are less important.

Figure 5:
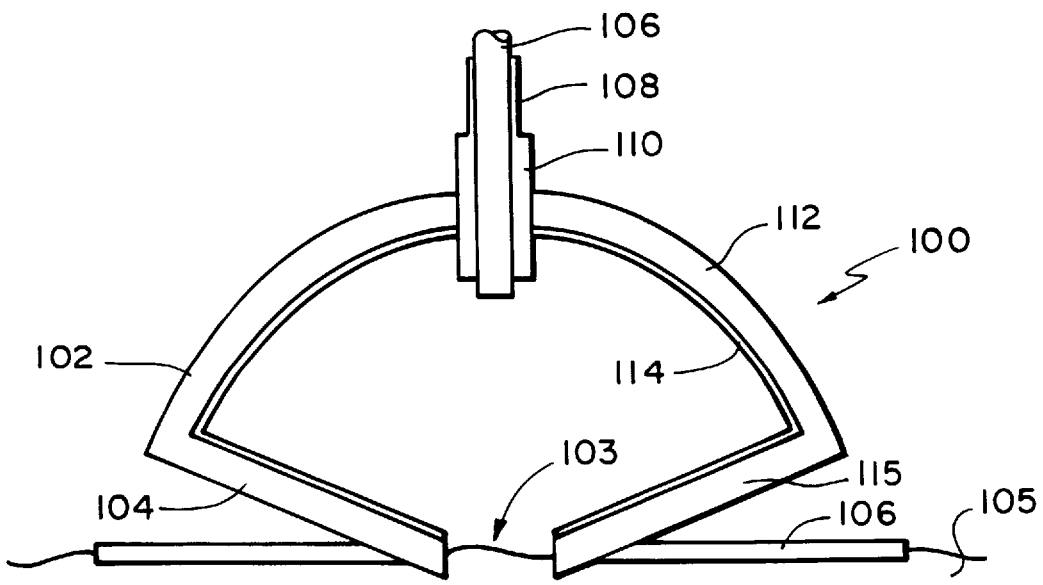
FIG. 5 is a cross-sectional side view of an irradiating device including a reflective housing featuring a hemispherical top portion and a tapered bottom portion.

FIG. 5 shows an another embodiment of the invention in which the reflective housing 112 of the irradiation device 100 is designed to capture and reflect the re-emitted light over the important region of approximately $\ominus=0°–60°$. The reflective housing includes a hemispherically shaped upper portion 102 and a conical lower portion 104 connected directly to a template 106. The template can be reduced in size or removed. In this configuration, the device, with its tapered lower portion occupying a relatively small area, is particularly effective in delivering radiation to hard-to-reach places.

The irradiated area 103 of tissue 105 is positioned substantially at the center of the upper portion 102 of the reflective housing 112. Preferably, the upper portion 102 extends at an angle of at least 60° from the angle of incidence of the input radiation. In this configuration, the reflective housing only contains reflective portions in regions where the contribution from re-emitted radiation intensity is high; no reflecting portion is present in the regions where the reflected radiation intensity is low, i.e., from about an angle of 60° to 90° from the angle of incidence. Note that the small amount of light which is re-emitted at these angles will be reflected by the lower portion 104 of the housing towards the upper portion 102, where it will then be reflected back towards the original area of irradiation.

The delivery handpiece 108 and input port 110 for this device are the same as those described for the embodiment of FIG. 1. Similarly, the reflective and substrate materials in this embodiment are the same as those described above. The figure shows a reflective coating 114 deposited on the inner surface of a substrate 115. Other types of reflective housings, such as those containing grooves, may also be used with the irradiation device.

Figure 6:
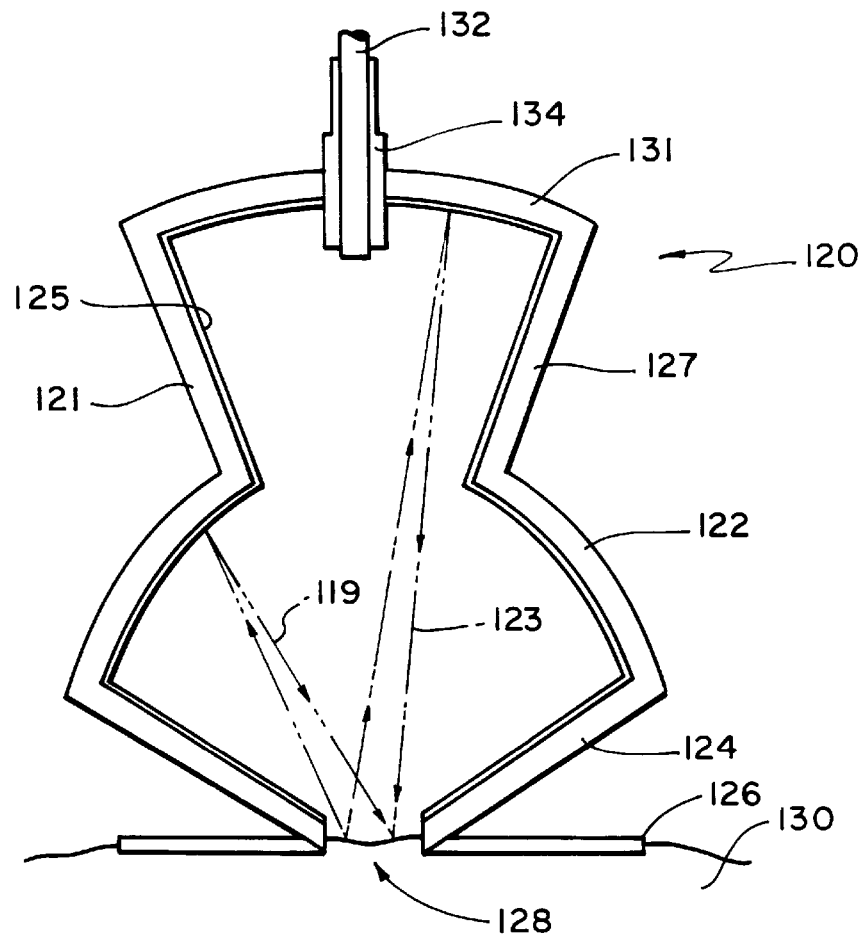
FIG. 6 is a cross-sectional side view of an irradiating device containing a reflective housing featuring two hemispherical top portions and a straight bottom portion.

Still other embodiments of the invention are shown in FIGS. 6–9. In FIG. 6, an irradiating device 120 features a reflective housing 121 including first 131 and second 122 hemispherical portions and first 127 and second 124 tapered portions. The reflective housing 121 is in contact with a template 126 and is configured to deliver re-emitted radiation to an area 128 of tissue 130. Each portion of the housing is coated with a reflective film 125 as in previous embodiments. As indicated by the arrows 119 and 123, re-emitted radiation is reflected by the coating back towards the originally irradiated region so that the amount of radiation delivered to the area 128 is increased. In this case, the first and second hemispherical portions have different diameters; the irradiated area 128 is positioned at the coincident centers of the two hemispheres. Separating the housing into first and second hemispherical portions results in a smaller amount of the re-emitted optical intensity irradiating the non-reflective region containing the fiber optic waveguide 132 and the input port 134. This is because re-emitted radiation spatially diverges after the incident beam irradiates the tissue, and thus the spatial concentration of radiation decreases as a function of distance from the irradiated region 128.

Figure 7:
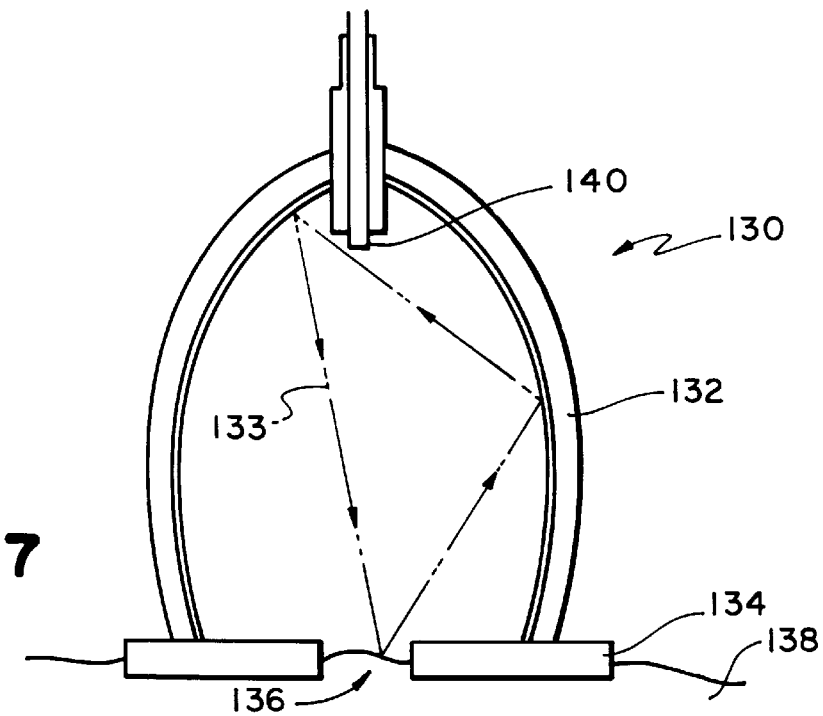
FIG. 7 is a cross-sectional side view of an irradiating device containing an elliptical reflective housing.

FIG. 7 shows another embodiment of the invention in which the irradiating device 130 includes a reflective housing 132 shaped as an ellipse. An area 136 of tissue 138 is irradiated with an incident beam delivered by the fiber optic waveguide 140. The elliptical housing is positioned with respect to a template 134 so that one of its foci is coincident with the irradiated area 136. In this way, as indicated by the arrow 133, re-emitted radiation is returned to the originally irradiated area after being reflected multiple times by the housing.

In the embodiments shown in FIGS. 6 and 7, the template connected to the housing can be replaced with a plate which is transparent to the incident radiation. Like the template, the transparent plate is used to position the device on the patient's tissue and facilitate alignment of the radiation. The plate is particularly effective in aligning radiation onto tissue containing rough or curved surfaces, such as the skin.

Figure 8:
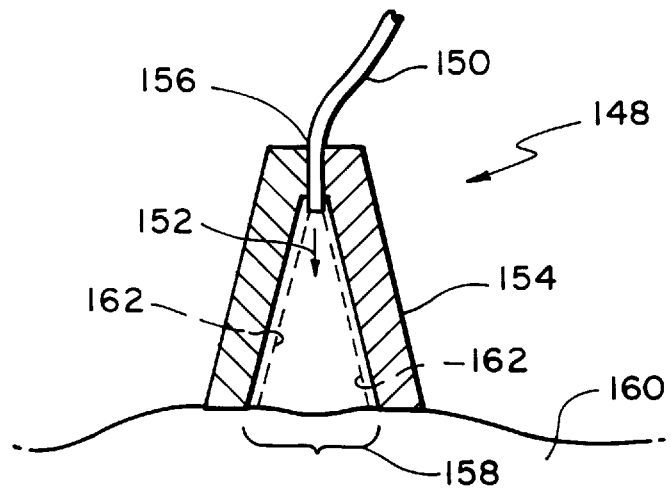
FIG. 8 is a cross-sectional side view of an irradiating device including a cone-shaped reflective housing; and, FIG. 9 is a side view of a irradiating device featuring a flat, optically transparent plate coated with a reflecting dielectric film.

FIG. 8 shows a cross-sectional view of an irradiating device 148 where an optical fiber 150 delivering optical radiation (indicated by the arrow 152) attaches directly to a cone-shaped, diffusely reflective housing 154. The housing 154 includes an upper opening 156 which houses the fiber, and a lower opening 158 placed in direct contact with a patient's tissue 160 (e.g., the skin). The housing 154 is preferably constructed entirely of a diffusely reflecting material, such as a white plastic, to form a highly reflecting cavity. Alternatively, the housing may be formed from a plastic, metal, glass material coated on its inner surface with a diffusely reflecting coating (e.g., a white paint or roughened metallic coating).

During operation, radiation emitted from the fiber 150 spatially diverges (typically at an angle of about 30°, as indicated by the dashed lines 162) until it impinges the tissue 160 and is absorbed. The height of the cone thus determines the radiation spot size on the tissue, as the radiation's divergence and area increase with cone height. Typically the cone height is chosen to be about 1.5 cm. As described above, a portion of the radiation impinging the tissue is randomly re-emitted and propagates back towards the housing 154. There, the radiation is either reflected back onto the tissue or onto another portion of the housing. These processes increase the gain, or total amount of radiation which is absorbed by the tissue. In theory, the reflection process continues until all the incident light is either absorbed by the tissue or is sent back through the fiber 150. It is therefore desirable to increase the ratio between the areas of the lower 158 and upper 156 openings, as this will increase the actual amount of light redirected towards the tissue.

Figure 9:
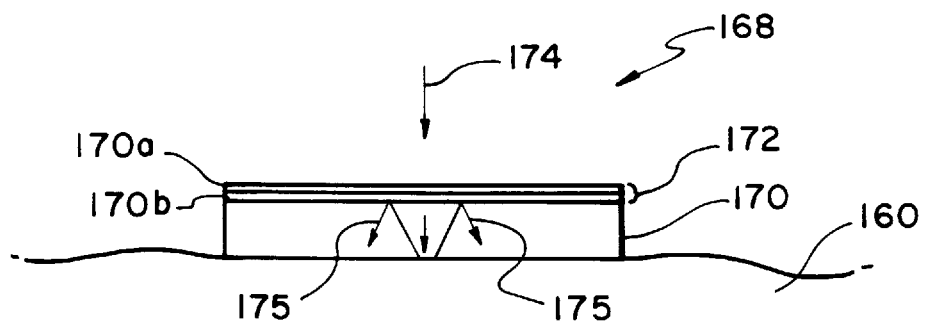

FIG. 9 shows another irradiating device 168 of the invention where the reflective housing consists of a optically transparent plate 170 coated on its upper surface with a dielectric coating 172. The plate 170, in turn, directly contacts the patient's tissue 160. As is well known in the art, the reflectivity of a dielectric coating depends on the angle and wavelength of the incident optical beam, and can maximized or minimized by varying the thickness and refractive index (i.e., the material composition) of the coating's dielectric layers 170a, 170b. The 'bandwidth' of the coating, i.e., the range of wavelengths or incident angles which are transmitted or reflected, depends on the refractive index and number of the layers.

For optimum performance, the device 168 preferably includes a narrow-band, high-efficiency coating which transmits normally incident radiation (indicated by the arrow 174) and radiation which deviates from normal by less than about 15°. After this radiation impinges the tissue 160, re-emitted radiation impinging the coating's bottom surface at angles greater than about 15° (indicated by the arrows 175), is reflected back towards the tissue by the coating to increase the gain. As is described above, re-emitted radiation typically leaves the tissue at an angle of about 45°. This process of reflecting re-emitted radiation continues until all the radiation is either absorbed by the tissue or is transmitted through the coating.

Other embodiments of the irradiating device of FIG. 9 are also possible. For example, the dielectric coating can be on the bottom surface of the glass plate. The plate can also be attached directly to a faceplate or handpiece for ease of use.

Therapies and Other Applications

The irradiation device can be used in combination with any known radiation-based therapy to increase the gain of the radiation. Examples of such therapies include optical removal of tatoos, port-wine stains, abnormal blood vessels, psoriatic skin, unwanted hair, pigmented lesions, skin cancers and other lesions treated by laser surgery, phototherapy, photochemotherapy or photodynamic therapy. Additional radiation-based therapies, particularly those used in dermatology, are described in Honigsmann et al., Dermatology in General Medicines, 3rd edition, T. B. Fitzpatrick et al. (eds.) 1728–1754 (1987), the contents of which are incorporated herein by reference.

During therapy, the opening of the template or the transparent plate is placed over the area to be irradiated. The therapy is then conducted according to standard procedures used in the optical and medical arts.

Because the effective amount of radiation which exposes the skin is increased using the irradiation device, it may be necessary to decrease the amount of radiation used during therapy. Typically, the fluence of the radiation is between about 0.1 and 100 W/cm$^2$. The spatial intensity profile of the radiation can be adjusted to vary the amount at radiation-induced heat delivered to the region of interest. Radiation spot diameters of between 10 microns and 1 cm are typically used.

A laser is the preferred light source for optical radiation. The laser is chosen according to the desired optical wavelength. Preferred lasers include ion, dye, solid-state (e.g., Nd:YAG, Nd:YLF, Ti:Sapphire) holmium, $CO_2$, metal-vapor, excimer, and diode lasers. Other light sources, such as fluorescent bulbs, may also be used. The light source may be continuous-wave or pulsed.

The irradiation device can also be used in non-medical applications to increase the gain of the incident radiation. For example, the device can be used with a laser to cut or process materials. The device may also be used to drive photochemical reactions in certain materials, such as light-sensitive films.

Still other embodiments are within the scope of the following claims.

What is claimed is:

1. A method for irradiating a material, said method comprising:
   delivering radiation to said material, the material partially re-emitting the delivered radiation,
   positioning a non-diffusive reflective surface to receive substantially all of the re-emitted radiation, and
   reflecting the re-emitted radiation to the material using a non-diffusive reflective surface.

2. The method of claim 1, wherein the re-emitted radiation is reflected, scattered, or reflected and scattered by the material.

3. The method of claim 1, wherein the reflective surface is a reflective housing positioned proximal to the material.

4. The method of claim 3, wherein the reflective housing comprises an irradiating device placed proximal to the material prior to said radiation delivering step.

5. The method of claim 3, wherein the reflective housing is substantially hemispherical in shape, and the material is positioned substantially near a center of the hemisphere.

6. The method of claim 3, wherein the reflective housing is substantially elliptical in shape, and the material is positioned substantially near a focus of the ellipse.

7. The method of claim 3, wherein the reflective housing is substantially cone-shaped and comprises a bottom opening, and the material is positioned near the bottom opening.

8. The method of claim 3, wherein the reflective housing is an optically transparent plate comprising a reflective coating which is substantially transparent to normally incident radiation and substantially reflects radiation incident at an angle, and the material is positioned in contact with a surface of the transparent plate.

9. The method of claim 3, wherein the reflective housing comprises a reflective coating for reflecting the re-emitted radiation.

10. The method of claim 3, wherein said reflective housing comprises an array of grooves configured to reflect the re-emitted radiation.

11. The method of claim 1, wherein the radiation is optical radiation.

12. The method of claim 1, wherein the material is a tissue.

13. The method of claim 12, wherein the tissue is human skin.

14. A device for use in delivering radiation from an external radiation source to a material, comprising:
    a reflective housing configured to receive radiation from the radiation source, said housing comprising an opening or surface for placement over a material and a non-diffusive reflective interior surface proximal to said opening or surface, said reflective interior surface being shaped to receive radiation re-emitted by the material and reflect the re-emitted radiation back onto the material.

15. The device of claim 14, wherein said non-diffusive reflective interior surface is a reflective film.

16. The device of claim 15, wherein said reflective film comprises a metallic or dielectric material.

17. The device of claim 14, wherein said reflective interior surface is an array of grooves formed in said reflective housing.

18. The device of claim 14, wherein said reflective interior surface is substantially hemispherical in shape and said opening is positioned at a center of the hemisphere.

19. The device of claim 14, wherein said reflective interior surface is substantially elliptical in shape and said opening is positioned at a focus of the ellipse.

20. The device of claim 14, wherein said reflective interior surface is substantially spherical in shape and said opening is disposed on a surface of the sphere.

21. The device of claim 14, wherein said reflective interior surface is substantially conical in shape and said opening is positioned at a base of the cone.

22. The device of claim 14, wherein said radiation source is connected to a fiber optic waveguide or an articulated arm.

23. A device delivering radiation to a material, comprising:
    a radiation source, said radiation source being a laser, and
    a reflective housing configured to receive radiation from said radiation source, said housing comprising an opening or surface for placement over a material and a non-diffusive reflective interior surface proximal to said opening or surface, said reflective interior surface being shaped to receive radiation re-emitted by the material and reflect the re-emitted radiation back onto the material.

24. A device for use in delivering radiation from a radiation source to a material, comprising
    an optically transparent plate, comprising a reflective coating on a surface, said reflective coating being disposed on the plate to transmit normally incident radiation from the radiation source, receive radiation re-emitted from a material, and reflect re-emitted radiation incident on the coating at an angle back onto the material.

25. The device of claim 24, wherein the reflective coating comprises a dielectric material.

26. The device of claim 25, wherein the reflective coating comprises multiple layers of dielectric materials.

27. A device for use in delivering radiation to a material, comprising a reflective housing configured to receive radiation from a radiation source, said housing comprising an opening or surface for placement over a material and a reflective interior surface proximal to said opening or surface, said reflective interior surface being shaped to receive radiation re-emitted by the material and reflect the re-emitted radiation back onto the material, wherein said reflective interior surface is an array of grooves formed in said reflective housing.

28. A device for use in delivering radiation to a material, comprising a reflective housing configured to receive radiation from a radiation source, said housing comprising an opening or surface for placement over a material and a reflective interior surface proximal to said opening or surface, said reflective interior surface being shaped to receive radiation re-emitted by the material and reflect the re-emitted radiation back onto the material, wherein said reflective interior surface is substantially hemispherical in shape and said opening is positioned at a center of the hemisphere.

29. A device for use in delivering radiation to a material, comprising a reflective housing configured to receive radiation from a radiation source, said housing comprising an opening or surface for placement over a material and a reflective interior surface proximal to said opening or surface, said reflective interior surface being shaped to receive radiation re-emitted by the material and reflect the re-emitted radiation back onto the material, wherein said reflective interior surface is substantially elliptical in shape and said opening is positioned at a focus of the ellipse.

30. A device for use in delivering radiation to a material, comprising a reflective housing configured to receive radiation from a radiation source, said housing comprising an opening or surface for placement over a material and a reflective interior surface proximal to said opening or surface, said reflective interior surface being shaped to receive radiation re-emitted by the material and reflect the re-emitted radiation back onto the material, wherein said reflective interior surface is substantially conical in shape and said opening is positioned at a base of the cone.

* * * * *